United States Patent [19]
Lindegren et al.

[11] Patent Number: 5,649,975
[45] Date of Patent: Jul. 22, 1997

[54] APPARATUS FOR PREVENTING A MEDICAL ELECTRODE ANCHORING ELEMENT FROM DAMAGING TISSUE DURING IMPLANTATION

[75] Inventors: Ulf Lindegren, Enskede; Måns Barsne, Stockholm, both of Sweden

[73] Assignee: Pacesetter AB, Solna, Sweden

[21] Appl. No.: 659,312

[22] Filed: Jun. 6, 1996

[30] Foreign Application Priority Data

Jun. 6, 1995 [SE] Sweden ................................. 9502058

[51] Int. Cl.$^6$ ................................................. A61N 1/05
[52] U.S. Cl. ........................ 607/126; 607/127; 128/642
[58] Field of Search ............................. 607/122, 126, 607/127, 130; 128/642; 604/263; 606/129

[56] References Cited

U.S. PATENT DOCUMENTS

| | | |
|---|---|---|
| 3,974,834 | 8/1976 | Kane . |
| 4,311,153 | 1/1982 | Smits . |
| 4,644,957 | 2/1987 | Bicciardelli et al. ................... 607/127 |
| 4,799,499 | 1/1989 | Bisping . |
| 4,827,910 | 5/1989 | Mayer et al. ........................... 128/642 |
| 5,261,417 | 11/1993 | Osypka ................................. 607/127 |
| 5,423,314 | 6/1995 | Schmid ................................. 128/642 |

FOREIGN PATENT DOCUMENTS

| | | |
|---|---|---|
| 0 003 948 | 9/1979 | European Pat. Off. . |
| 0219608 | 4/1987 | European Pat. Off. ........ A61N 1/05 |
| PS 33 00 050 | 9/1991 | Germany . |

OTHER PUBLICATIONS

Mugica et al., "The Screw-in Catheter for Long-Term Endocaridial Pacing," La Nouvelle Presse Medicale, 06 Mar. 1976, 5 No. 10 p. 654.

*Primary Examiner*—Jeffrey R. Jastrzab
*Attorney, Agent, or Firm*—Hill, Steadman & Simpson

[57] ABSTRACT

An apparatus for preventing an anchoring element on the distal end of an implantable medical electrical conductor from coming into contact with and damaging the wall of a body cavity during advancement of the conductor into the cavity has a sleeve element attachable to the outer surface of the distal end of the conductor to enclose the entire length of the anchoring element, and a pulling element attached to the distal end of the sleeve element. Pulling on the pulling element from the proximal end of the conductor retracts the sleeve element after introduction of the conductor has been concluded, to expose the anchoring element for active fixation to adjacent body tissue. An implantable electrode cable equipped with such an end protector.

7 Claims, 1 Drawing Sheet

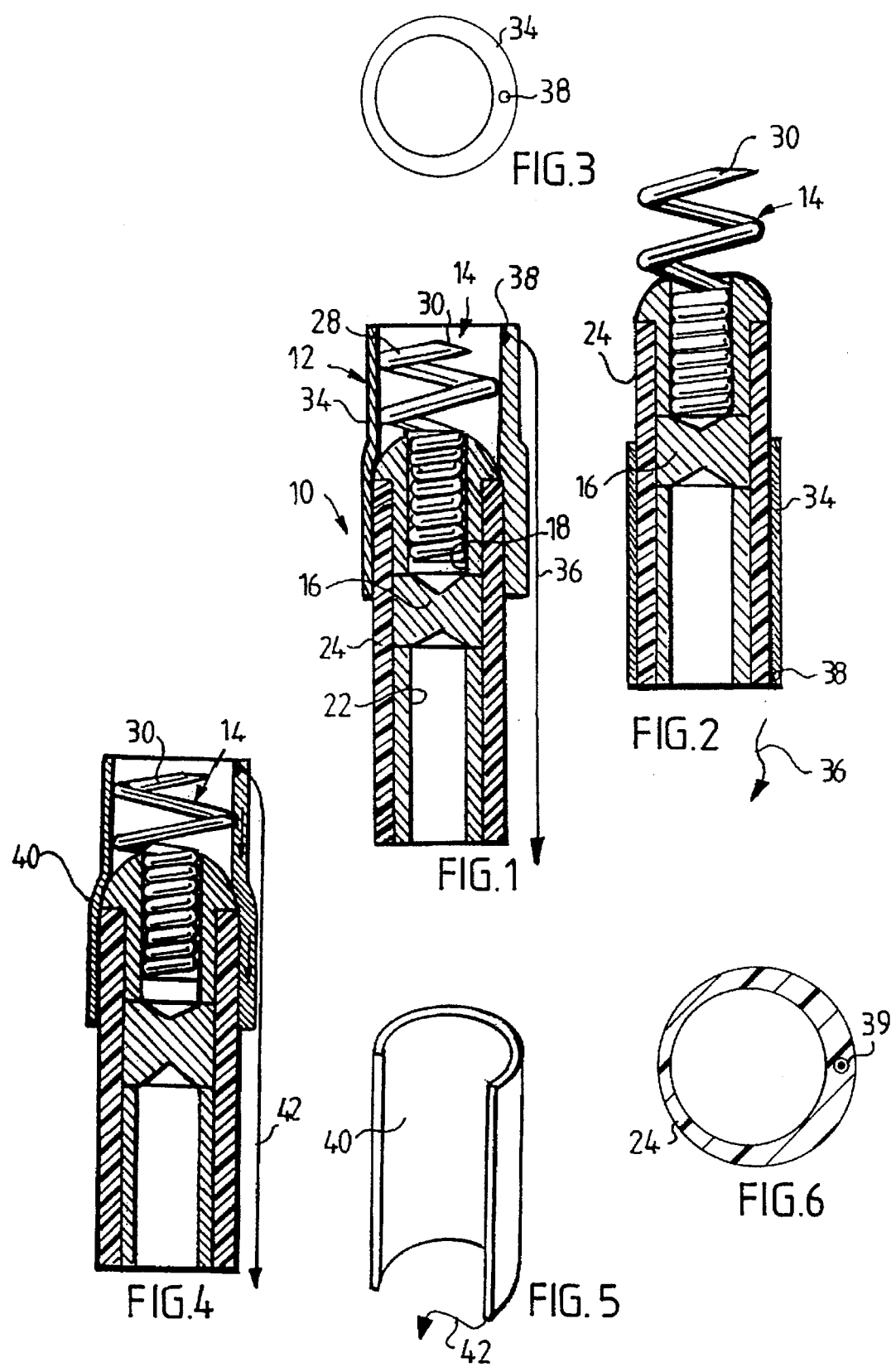

APPARATUS FOR PREVENTING A MEDICAL ELECTRODE ANCHORING ELEMENT FROM DAMAGING TISSUE DURING IMPLANTATION

BACKGROUND OF THE INVENTION

1. Field of the Invention

The present invention relates to a device for preventing an anchoring element protruding from a distal end of an implantable electrical conductor from coming into contact with and damaging the wall of a body cavity during the conductor's advancement into that cavity.

2. Description of the Prior Art

An implantable electrical conductor, i.e., an electrode cable, is typically designed for connection at its proximal end to a medical device, such as a pacemaker, and its other, distal end is to be affixed to a site in a ventricle or atrium of the heart. Such a conductor can, following intravenous advancement into the heart, be passively or actively affixed to the heart wall to transmit electrical impulses to heart muscle, thereby stimulating the muscle to contract or sense the heart's intrinsic activity as a means of controlling the pacemaker's operation. In "passive" fixation of the distal end of the electrode cable, the end is usually equipped with small fins or tines to facilitate anchoring of the end in the heart wall without penetrating the heart wall.

"Active" fixation of a cable end to the atrial wall is preferred for achieving rapid, forced fixation of the distal end of the electrode cable to the heart wall in the implantation of electrode cable, e.g. when the end of the cable is to be J-shaped and press against an atrial wall. The end of the electrode is then equipped with an anchoring means which can be driven into wall tissue during implantation. The procedure can be monitored by fluoroscopy to ensure that the cable end reaches the correct position.

One anchoring means commonly used for this purpose is in the form of a helical screw with a pointed tip. Electrode ends of this kind require active rotation of the anchoring means in order to screw the tip and a portion of the helical screw into the heart wall. In arrangements in which the helical screw can rotate freely at the end of the electrode cable, the helical screw can be rotated with the aid of a stylet, inserted from the proximal end of the electrode cable and made to grip a polygonal recess at the proximal end of the helical screw (or its mount), and screwed into and anchored in heart wall, the end of the electrode pressing against the heart wall.

In order to keep the pointed tip of the helical screw from coming into contact with and damaging the walls of veins and the heart during the electrode cable's implantation, the aforementioned freely rotating helical screw can be initially retracted into a protective recess at the end of the electrode cable and not deployed, with the aid of the stylet, until it reaches the intended anchoring site just before the helical screw is screwed in.

In another type of anchoring means for active fixation of the end of the electrode in the heart wall, the helical screw is rigidly mounted on the distal end of the electrode and protrudes freely from same. In this instance, the helical screw must be provided with some form of protection to keep the tip of the helical means from damaging venous and heart walls during implantation of the electrode cable. The entire electrode cable, including its sheath, must then be rotated to drive the helical screw into the heart wall.

Different ways of preventing such rigidly mounted, protruding helical screw elements from causing damage during cable introduction have been previously proposed. For example, U.S. Pat. No. 4,827,940 discloses a body, covering the helical screw element, which dissolves in body fluid within a few minutes, whereupon the helical screw can be screwed into the heart wall.

Another proposal is disclosed in U.S. Pat. No. 3,974,834, in which a compressible, bellows-like sleeve on the distal end of the electrode cable protects the helical screw during intravenous advancement of the electrode cable, and is compressed when pressed against the heart wall, enabling the tip of the helical means to gain a footing for screwing into the heart wall.

German OS 3 300 050 shows a version of active electrode fixation (FIG. 4) in which a rounded, tensioned electrode body can be kept extended out of an enclosing helical screw, preventing the tip of the helical screw from damaging the venous wall during intravenous advancement of the electrode cable into the heart.

Furthermore, U.S. Pat. No. 5,261,417 discloses a cardiac pacemaker lead having a protection jacket attached to the tip and a portion of the adjacent convolution of a helix fixing element to prevent damage to the tissue during advancement of the lead through blood vessels and into the heart. The jacket is retractable by a length of wire or cord, either along the external surface of the sheath or through an axial passageway of the conductor after the implantation. Either way, due to the attachment of the jacket to the proper tip portion of the helix element, the jacket may be susceptible to unintentional loosening from the tip portion during the advancement of the lead through the blood vessels.

SUMMARY OF THE INVENTION

An object of the present invention is to achieve a simplified end protector for an anchoring means on the distal end of an implantable electrode cable, which is securely attached thereto during the insertion and which can be quickly retracted therefrom in order to expose the distal end of the electrode and permit reliable and strong application of the end of the cable to the heart wall after the anchoring means has been screwed in.

The above object is achieved according to the invention, in an apparatus having a sleeve element with a proximal end portion adapted to be attached to the distal end of the conductor so as to enclose the entire length of the anchoring element protruding from the distal end of the conductor, and an elongated pulling element attached to the distal end portion of the sleeve element. The pulling element can then be arranged to either tear off the sleeve element for removal of the sleeve element together with the pulling element, or turn the sleeve inside out to expose the anchoring element, the pulling element then being arranged to be detached from the sleeve element after the latter has been turned inside out.

The invention also relates to an implantable electrode cable which is equipped with an end protector according to the above.

DESCRIPTION OF THE DRAWINGS

FIG. 1 shows a section of a first embodiment of the end protector according to the present invention in a position providing protection for an anchoring element.

FIG. 2 shows the end protector in FIG. 1 after it has been turned inside out to expose the free end section of the anchoring element.

FIG. 3 shows a schematic plan view of the protective sleeve in FIGS. 1 and 2.

FIG. 4 shows a detachable version of the end protector according to the invention.

FIG. 5 shows the protective sleeve in FIG. 4 in the detached state.

FIG. 6 is a cross-section through the external sheath of an implantable electrode cable with a channel for the pulling element.

DESCRIPTION OF THE PREFERRED EMBODIMENTS

FIG. 1 shows the distal end section 10 of an electrode cable intended for active fixation in a cavity of the heart and which is equipped with a device 12, according to a first embodiment of the invention, to protect a pointed anchoring means 14 on the end of the electrode cable while the electrode cable is being advanced into the heart. The end portion 10 has an electrode sleeve 16 with a first, distally located indentation 18 to fit an attachment part 20 of the anchoring assembly 14 and a second, proximally located internal opening 22 for a helically wound electrical conductor (not shown).

The sleeve 16 and conductor are enclosed in a sheath of insulating material 24.

The anchoring assembly 14 also has a "corkscrew-shaped" fixing element 28 with a sharp-pointed tip 30 which protrudes from the distal, electrode contact end 26 of the sleeve 16. The anchoring means 14 can be coated with an insulating layer of e.g. perylene.

A protective device 12 is arranged to prevent the pointed tip 30 fixing element 28 of the anchoring assembly 14 from damaging the walls of the vein and heart during intravenous introduction of such an electrode cable for active fixation to a heart wall.

FIGS. 1-3 show a first embodiment of the protective device according to the invention, wherein the device includes an elastic sleeve element 34 which is forced onto the distal end portion 10 of the electrode cable, and a pulling element 36 in the form of a wire attached at a point 38 in a distal part of the sleeve element 34. The thickness of the walls of the sleeve element 34 is preferably asymmetrical, the attachment point 38 for the pulling element 36 being located in the thick-walled section, as shown in FIG. 3, to facilitate turning the sleeve element 34 inside out when the pulling element 36 is pulled. After the electrode cable has been advanced to the desired anchoring site in the heart, e.g., the right atrium, with the aid of a conventional stylet, the protective device 12 is removed from the anchoring element 28.

FIG. 2 shows the position of the sleeve element 34 prior to fixation but after the sleeve means has being pulled inside out by the pulling element 36, the latter being arranged to detach from the attachment site 38 after being further pulled, so it can be removed from the heart and the traversed vein. The sleeve element 34 is thereby left behind on the end section 10 of the electrode cable. Then, the entire electrode sheath 24 is rotated to screw in the fixing element 28 of the anchoring assembly 14 into the wall of the heart.

In the embodiments according to FIGS. 1-3, it may be appropriate for the pulling element 36 to run through a protective channel 39 in the external sheath 24 of the electrode cable, as shown in FIG. 6.

An additional embodiment of the protective device according to the present invention is shown in FIGS. 4 and 5 in which the sleeve element 40 is designed to be torn off axially, after the electrode cable has been advanced into the heart, by the attached pulling wire 42, leaving the pulling wire 42 in this instance behind on the sleeve element 40 (FIG. 6) to retract the sleeve element 40 after the distal end of the electrode cable has been positioned in the heart.

Although modifications and changes may be suggested by those skilled in the art, it is the intention of the inventor to embody within the patent warranted hereon all changes and modifications as reasonably and properly come within the scope of his contribution to the art.

We claim as our invention:

1. In an implantable medical electrode cable containing an electrical conductor and having a first end from which an anchoring element protrudes, the improvement of an apparatus for preventing said anchoring element protruding from said first end from damaging tissue during advancement of said lead into a body, said improvement comprising:
    a sleeve element disposed at said first end of said cable and enclosing an entire length of said anchoring element protruding from said first end, said sleeve element having a free end; and
    pulling means, attached to said free end of said sleeve element and accessible from a second end of said conductor, opposite said first end, for retracting on said sleeve element to expose said anchoring element after said cable has been advanced into said body to a selected location.

2. The improvement of claim 1 wherein said sleeve element is detachably mounted to said first end of said cable, and wherein said pulling means comprises means for detaching said sleeve element from said first end.

3. The improvement of claim 1 wherein said sleeve element is attached at said first end of said cable and wherein said pulling means comprises means for turning said sleeve element inside out to expose said anchoring element and said pulling means thereafter detaching from said sleeve element.

4. The improvement of claim 3 wherein said sleeve element comprises a cylindrical wall with a non-uniform wall thickness having a thickest portion, and wherein said pulling means is attached to said sleeve element at said thickest portion.

5. The improvement of claim 1 wherein said cable has an external insulating sheath containing said conductor, and wherein said pulling element runs along an exterior of said sheath.

6. The improvement of claim 1 further comprising a sheath containing said electrical conductor, said sheath having sheath wall with a channel therein running along a longitudinal length of said sheath, and wherein said pulling means is disposed in said channel.

7. An implantable electrode cable comprising:
    an insulating sheath having a distal end and a proximal end;
    an electrical conductor disposed in said insulating sheath and having an anchoring element protruding from said distal end of said sheath;
    a sleeve element mounted at said distal end of said sheath and completely enclosing said anchoring element, said sleeve element having a free end spaced from said distal end of said sheath; and
    pulling means, attached to said distal end of said sleeve element, and accessible from said proximal end of said sheath, for acting on said sleeve element to expose said anchoring element after advancement of said distal end of said sheath to a selected location in a body.

* * * * *